United States Patent
Birnkrant et al.

(10) Patent No.: US 9,729,831 B2
(45) Date of Patent: Aug. 8, 2017

(54) WIRELESS SURGICAL LOUPE

(71) Applicant: SONY CORPORATION, Tokyo (JP)

(72) Inventors: Marc Birnkrant, Poway, CA (US); Allen Poirson, Nevada, CA (US); Kelly Davis, San Diego, CA (US); Kojiro Umemura, Tokyo (JP); Hitoshi Namba, Tokyo (JP)

(73) Assignee: Sony Corporation, Tokyo (JP)

( * ) Notice: Subject to any disclaimer, the term of this patent is extended or adjusted under 35 U.S.C. 154(b) by 339 days.

(21) Appl. No.: 13/689,603

(22) Filed: Nov. 29, 2012

(65) Prior Publication Data

US 2014/0146153 A1 May 29, 2014

(51) Int. Cl.
| | |
|---|---|
| *H04N 7/18* | (2006.01) |
| *A61B 17/00* | (2006.01) |
| *A61B 90/00* | (2016.01) |
| *A61B 90/50* | (2016.01) |

(52) U.S. Cl.
CPC .............. *H04N 7/18* (2013.01); *A61B 90/361* (2016.02); *A61B 2017/00221* (2013.01); *A61B 2017/00734* (2013.01); *A61B 2090/3616* (2016.02); *A61B 2090/502* (2016.02)

(58) Field of Classification Search
CPC ...... A61B 19/5212; A61B 2017/00221; A61B 2019/521; H04N 7/18
See application file for complete search history.

(56) References Cited

U.S. PATENT DOCUMENTS

| | | | |
|---|---|---|---|
| 6,304,259 B1* | 10/2001 | DeStefano | G06F 17/30014 706/50 |
| 6,847,336 B1* | 1/2005 | Lemelson | A61B 1/00048 345/8 |
| 7,367,809 B2 | 5/2008 | Takahashi | |
| 2006/0079752 A1 | 4/2006 | Anderl et al. | |
| 2007/0184422 A1* | 8/2007 | Takahashi | G06F 19/3437 434/262 |
| 2008/0180521 A1* | 7/2008 | Ahearn | 348/42 |
| 2009/0168166 A1* | 7/2009 | Obrebski | G02B 21/0012 359/466 |
| 2009/0268010 A1* | 10/2009 | Zhao | A61B 1/00009 348/45 |
| 2010/0095604 A1* | 4/2010 | Newkirk | E04F 19/08 52/79.1 |

(Continued)

FOREIGN PATENT DOCUMENTS

| | | |
|---|---|---|
| EP | 0048181 A2 | 9/1981 |
| JP | 2003204972 A | 7/2003 |

(Continued)

OTHER PUBLICATIONS

Office Action from Russian Application No. 2013149280.

(Continued)

*Primary Examiner* — Thai Tran
*Assistant Examiner* — Christopher T Braniff
(74) *Attorney, Agent, or Firm* — Haverstock & Owens LLP

(57) ABSTRACT

A wireless surgical loupe enables a user to use the wireless loupe to perform a procedure, transmit information acquired by the wireless loupe and display patient information on a wireless loupe display. The transmitted information is able to be used to aid the operating room procedure, enhance education and be recorded for later use.

21 Claims, 11 Drawing Sheets

(56) References Cited

U.S. PATENT DOCUMENTS

| | | | |
|---|---|---|---|
| 2010/0182418 A1* | 7/2010 | Jess | G02B 21/0012 |
| | | | 348/79 |
| 2011/0043612 A1 | 2/2011 | Keller et al. | |
| 2011/0145978 A1* | 6/2011 | Harbin | G02B 23/125 |
| | | | 2/209.13 |
| 2012/0197102 A1* | 8/2012 | Hanebuchi | A61B 3/13 |
| | | | 600/398 |

FOREIGN PATENT DOCUMENTS

| | | |
|---|---|---|
| JP | 2006-297060 A | 11/2006 |
| JP | 2009098570 A | 5/2009 |
| JP | 2010-142641 A | 7/2010 |
| KR | 1020060127251 A | 12/2006 |
| WO | 2010144426 A1 | 12/2010 |
| WO | 2011002209 A2 | 6/2011 |

OTHER PUBLICATIONS

Rafael C. Gonzalez et al. "Digital Image Processing" Second Edition, Moscow, 2005 pp. 213-218, (See pp. 137-141 of the enclosed English language analog)Prentice Hall, Upper Saddle River, New Jersey 07458.
Office Action and English translation from Korean Patent Application No. 10-2013-0137658.

* cited by examiner

WIRELESS SURGICAL LOUPE

FIELD OF THE INVENTION

The present invention relates to the field of medical devices. More specifically, the present invention relates to surgical loupes.

BACKGROUND OF THE INVENTION

Surgeons in many specialties commonly use loupes when doing surgery on delicate structures. The loupes used by surgeons are mounted in the lenses of glasses and are custom made for the individual surgeon, taking into account their corrected vision, interpupillary distance and desired focal distance. Some loupes are attached to a helmet or other device worn on the head. Multiple magnification powers are available. They are most commonly used in plastic surgery, orthopedics surgery, microvascular surgery, and tendon repair surgery.

SUMMARY OF THE INVENTION

A wireless surgical loupe enables a user to use the wireless loupe to perform a procedure, transmit information acquired by the wireless loupe and display patient information on a wireless loupe display. The transmitted information is able to be used to aid the operating room procedure, enhance education and be recorded for later use.

In one aspect, a method of utilizing a wireless loupe comprises wearing the wireless loupe, displaying patient information on a display of the wireless loupe and performing a procedure while wearing the wireless loupe. The wireless loupe is configured for automatically transmitting a signal including information acquired through a wireless loupe lens and the patient information to an external device. The method further comprises presenting the signal for educational purposes.

In another aspect, a method of utilizing a wireless loupe comprises acquiring and receiving content at the wireless loupe, displaying the content on a wireless loupe display, transmitting the content to an image processing system and distributing the content from the image processing system. The content comprises acquired content acquired through a lens and received content received from a separate medical device. Acquiring the content includes receiving a signal of a subject. Receiving the content includes receiving monitoring information from one or more monitoring devices. The monitoring information is displayed on the wireless loupe display. The monitoring information includes patient statistics. Acquiring the content includes splitting the content using a half mirror, wherein a first portion of the content is viewable by a person and a second portion of the content is captured by a sensor. Receiving the content includes displaying received content from a medical device and splitting the content using a half mirror, wherein a first portion of the content is viewable by a person and a second portion of the content is captured by a sensor. The image processing system records the content. Transmitting is performed wirelessly. Distributing the content includes sending the content to screens for educational purposes.

In another aspect, a wireless loupe device comprises a lens, a half mirror for splitting information received from the lens into a first portion and a second portion, wherein the first portion goes to a user's eye and the second portion goes a sensor and a wireless communication component for transmitting the information acquired at the sensor. The half mirror comprises translucent mirror technology. The wireless loupe device further comprises a projection system for projecting patient information on a display which is split and reflected by the half mirror to the user's eye and received at the sensor.

In another aspect, a wireless loupe system comprises a wireless loupe device for acquiring a first content, receiving a second content and transmitting the first content and the second content, wherein the first content includes information received through a lens of the wireless loupe device and the second content includes patient information from one or more monitoring devices and an imaging system for receiving the first content and the second content. The imaging system is further for processing and storing the first content and the second content. The wireless loupe system further comprises an internal network for distributing the first content and the second content to a medical recording device. The wireless loupe system further comprises an external network for distributing the first content and the second content to one or more external screens. The wireless loupe device presents a through-the-lens view and the patient information.

DETAILED DESCRIPTION OF THE PREFERRED EMBODIMENT

A wireless surgical loupe is a digital version of an optical loupe. By adding digital electronics, the surgical loupe is able to capture and transmit the doctor's "through-the-lens" image to the rest of the operating room or to a remote location. Patient-related information is also able to be utilized to record a procedure for patient records or hospital records. The wireless surgical loupe also enables telemedicine, remote teaching and training. For those in the operating room, this enables a much more efficient or as the team is able to better anticipate the doctor's needs and instrument contamination is able to be better contained. If the power fails in the operating room, the loupe still works as 70% of the light will still go through.

Figure 1:
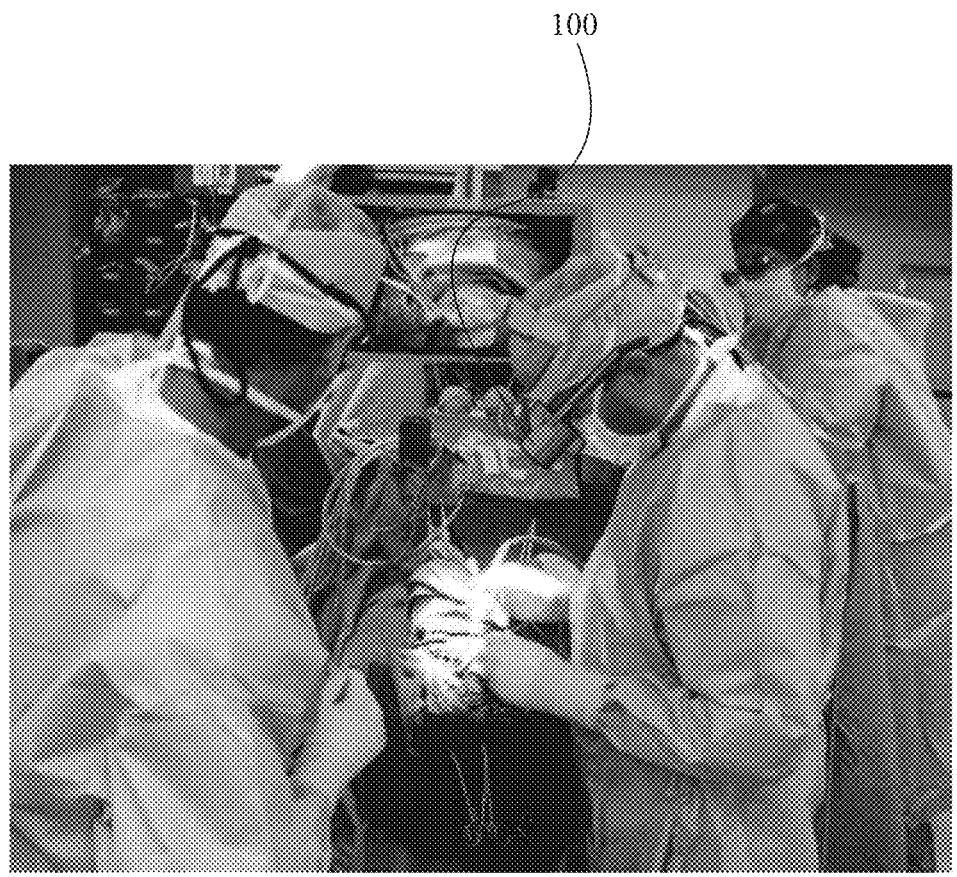
FIG. 1 illustrates an operating room with a doctor wearing a wireless surgical loupe according to some embodiments.

FIG. 1 illustrates an operating room with a doctor wearing a wireless surgical loupe according to some embodiments.

Figure 2:
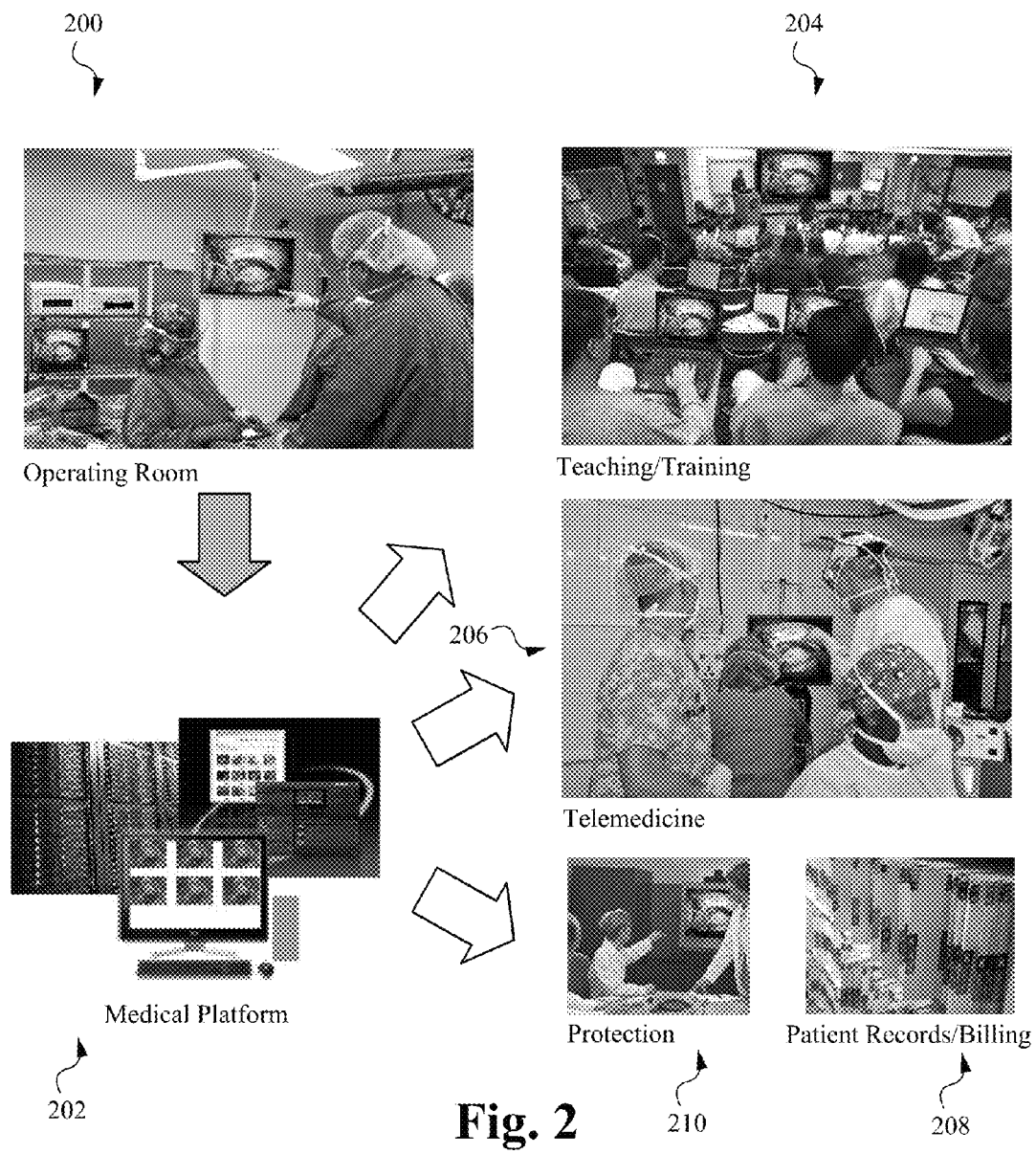
FIG. 2 illustrates a coordination of the wireless surgical loupe with applications according to some embodiments.

FIG. 2 illustrates a coordination of the wireless surgical loupe with applications according to some embodiments. In the operating room 200, a surgeon uses the wireless surgical loupe to perform a procedure. The information received from the wireless surgical loupe is sent to a medical platform 202. The medical platform 202 includes servers for storing the data, monitors for presenting the data and remote computers (e.g., desktops and smart phones) for receiving the data. The data is able to be used for teaching and training 204, telemedicine 206, patient records and billing 208, and protection 210.

Figure 3:
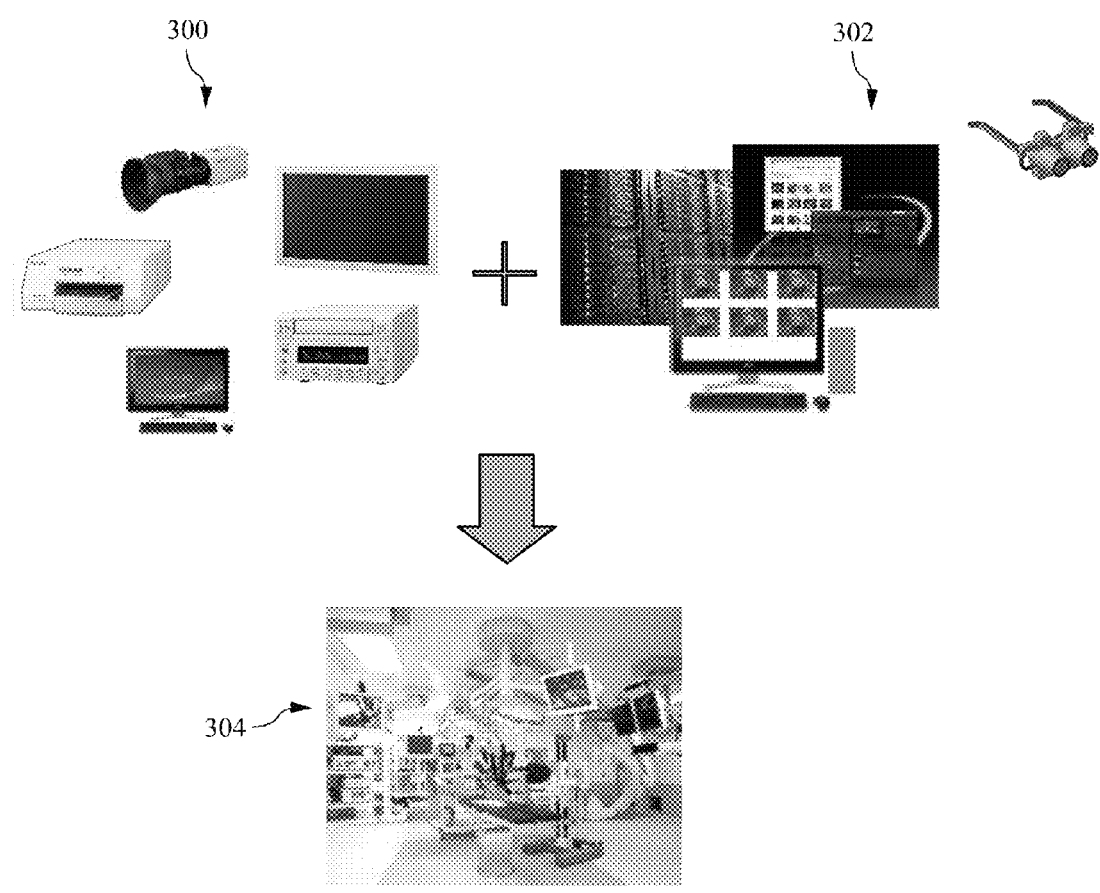
FIG. 3 illustrates an exemplary wireless loupe system according to some embodiments.

FIG. 3 illustrates an exemplary wireless loupe system according to some embodiments. I/O devices 300 include a camera, a monitor, a television, a printer and a video recorder. Computing devices 302 include servers, computing devices and networks (e.g., the cloud). When the I/O devices 300 and the computing devices 302 are combined with the wireless loupe 100, a wireless loupe system 304 is able to improve the operating room and other aspects of the medical field.

The wireless surgical loupe will simplify operating room setup and workflow by eliminating microscope setup and maximizing assistants' efficiency by anticipating a next action. A recording procedure is enabled when and where required. Telemedicine and remote training is enabled. Service enhancements are also possible (e.g., including the video in a patients record). The teaching environment is also improved by monitoring student surgeries, reviewing case studies and conducting surgical planning.

The targeted surgery disciplines are neurosurgery, orthopedics, cardiovascular, otolaryngology and any others. The wireless surgical loupe is able to provide image enhancement (e.g., filter blood vessels to stand out, highlight suspicious tissue), enable image fusion and stereotactic surgery, reduce cognitive load (e.g., vital signs are superimposed in the field of view) and reduce the error rate.

Figure 4:
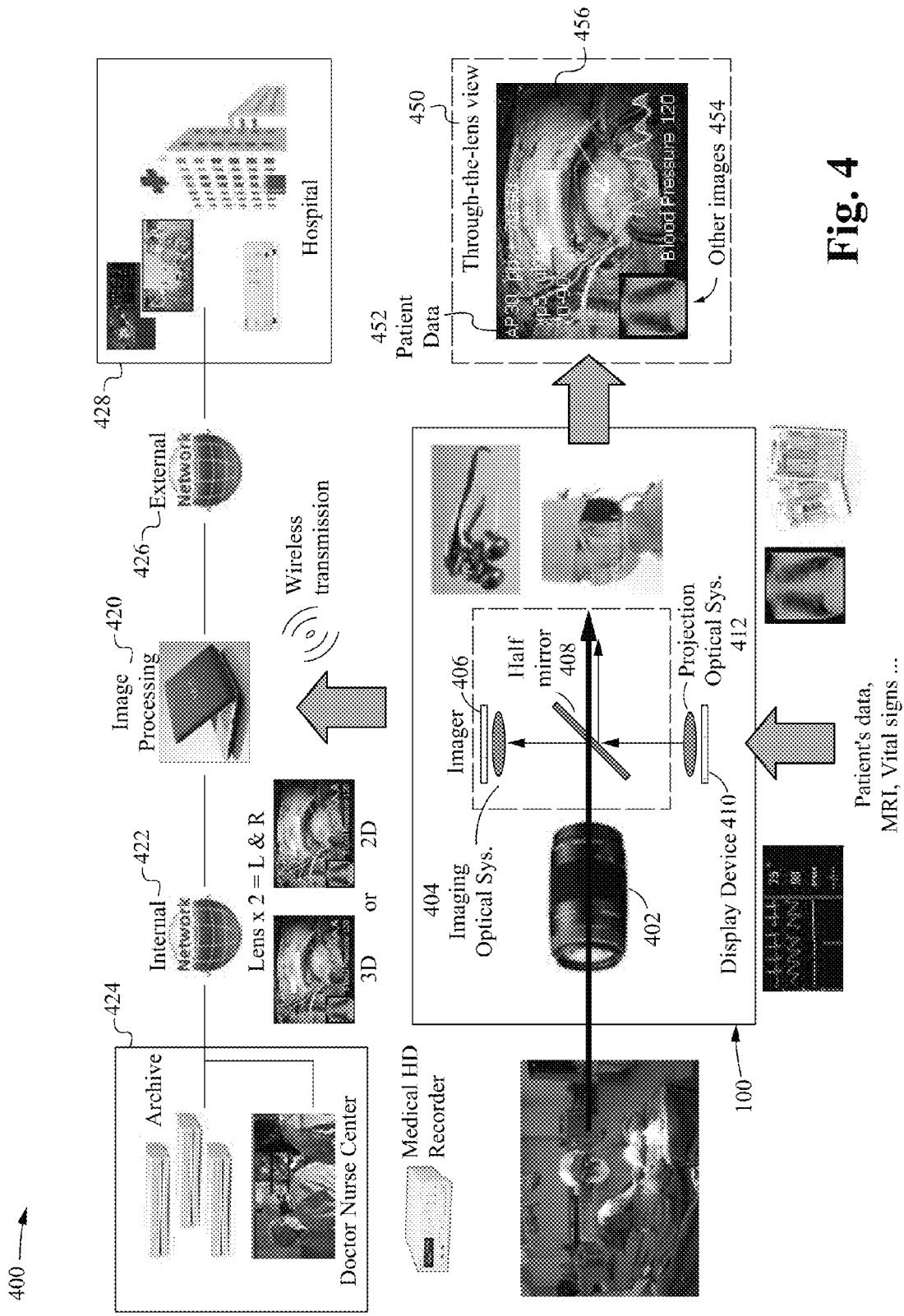
FIG. 4 illustrates a diagram of a wireless surgical loupe system according to some embodiments.

FIG. 4 illustrates a diagram of a wireless surgical loupe system according to some embodiments. The wireless surgical loupe system 400 includes a wireless loupe 100, an image processing system 420, an archiving system 426 and an external system 428. The wireless loupe 100 includes a lens 402, an optical imaging system 404, an imager 406, a half mirror 408, a display device 410 and a projection optical system 412.

The lens 402 is able to be any type of lens. In some embodiments, the wireless loupe 100 includes a plurality of lenses (e.g., one for each eye of the surgeon). Light is received through the one or more lenses 402, and a majority of the light passes through the half mirror 408 to the surgeon's eye. In some embodiments, 70% or more of the light passes through the half mirror 408 to the surgeon's eye. The remainder of the light is reflected by the half mirror 408 to the imaging optical system 404 which directs the light to the imager 406. The imaging optical system 404 is able to include one or more lenses for focusing the light onto the imager 406. The imager 406 captures the light. The captured information is able to be wirelessly transmitted to the image processing system 420 for presentation on external screens, storage in a medical records database or any other use.

The display device 410 receives patient data 452 such as vital information from other medical equipment. The patient data 452 is able to be received wirelessly. The patient data 452 is able to be received from other devices such as a heart monitor, blood pressure monitor and any other devices. The projection optical system 412 projects the patient information to the half mirror 408 which directs a portion of the projection to the surgeon's eye and another portion of the projection to the imaging optical system 404 and imager 406 for capture and transmission to be recorded or presented on an external screen. The patient information is able to be presented in a through-the-lens view 450 such as by using a heads up display. The view 450 includes patient data 452 (e.g., vital signs), additional images 454 and the through-the-lens view 456.

The information acquired by the imager 406 and wirelessly transmitted to the image processing system 420 is able to be transmitted through an internal network 422 to archive devices 424 and/or an external network 426 to hospital devices 428.

Figure 5:
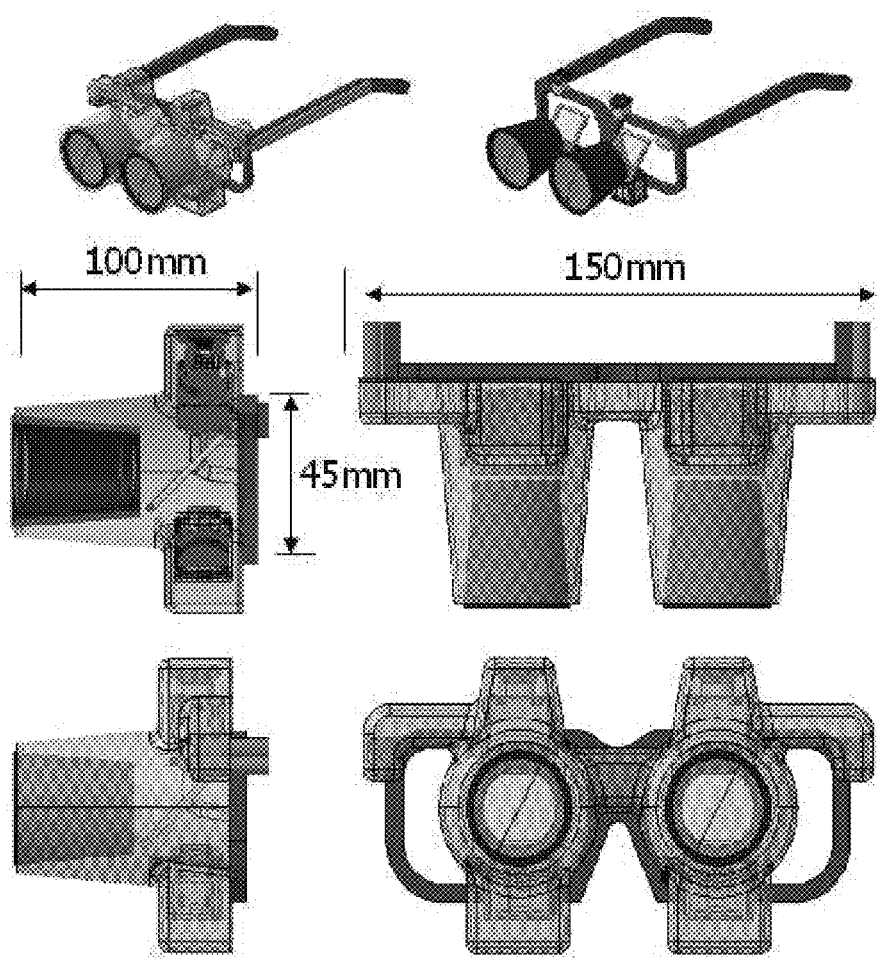
FIG. 5 illustrates several views of a wireless loupe according to some embodiments.

FIG. 5 illustrates several views of a wireless loupe according to some embodiments. The views include a left view, a right view, a top view, a front view and perspective views. The wireless loupe is able to be any size; however, specifically shown, the dimensions of the loupe are 100 mm×150 mm×45 mm.

Figure 6:
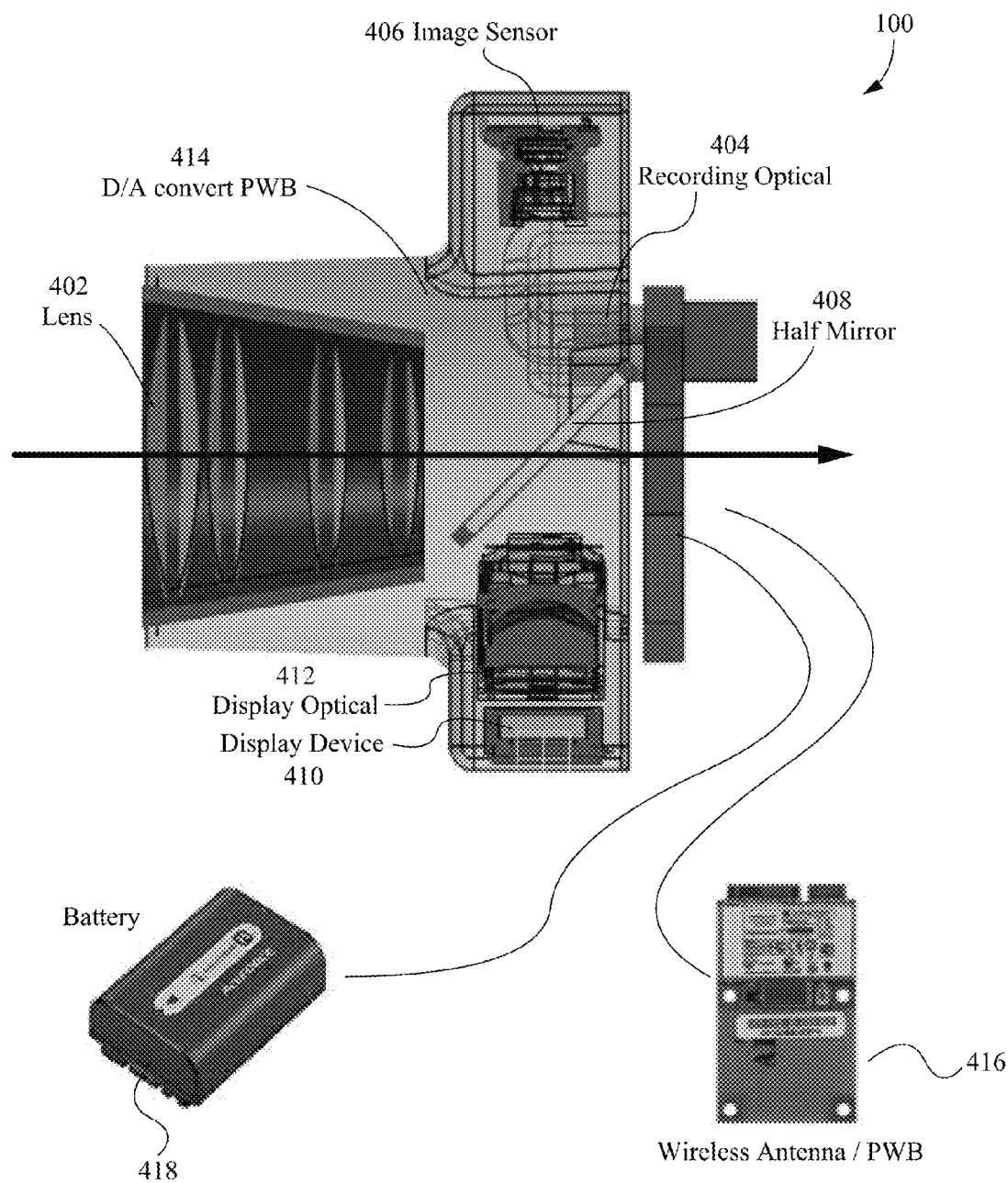
FIG. 6 illustrates a view of the components of a wireless loupe according to some embodiments.

FIG. 6 illustrates a view of the components of a wireless loupe according to some embodiments. The wireless loupe 100 includes a lens, a recording optical device 404 (also referred to as optical imaging system), an image sensor 406, a half mirror 408, a display device 410, a display optical sensor 412 (also referred to as a projection optical system), a DA/covert PWB 414, a wireless antenna/PWB 416 and a battery 418. The lens 402 is able to be any type of lens, for example the lens 402 includes 4 sets of convex and concave lenses for magnifying a signal. In some embodiments, the magnification of the lens 402 is fixed, and in some embodiments, the magnification is able to be varied. The signal passes through the half mirror 408, for the operator (e.g., surgeon) to see (e.g., to perform an operating procedure). The split signal is received by the recording optical device 404 and image sensor 406. The recorded signal is then able to be transmitted by the wireless antenna 416. The display device 410 and display optical sensor 412 are used to send patient data (e.g., vital signs) to the operator of the wireless loupe 100. In some embodiments, the wireless loupe 100 receives the patient data wirelessly from monitoring devices.

The half mirror 408 is able to be any half mirror such as a translucent mirror technology utilizing polycarbonate film, sputtering coating technology and/or multi-layer coating. The image sensor 406 is able to be any sensor such as a backside illumination CMOS.

Figure 7:
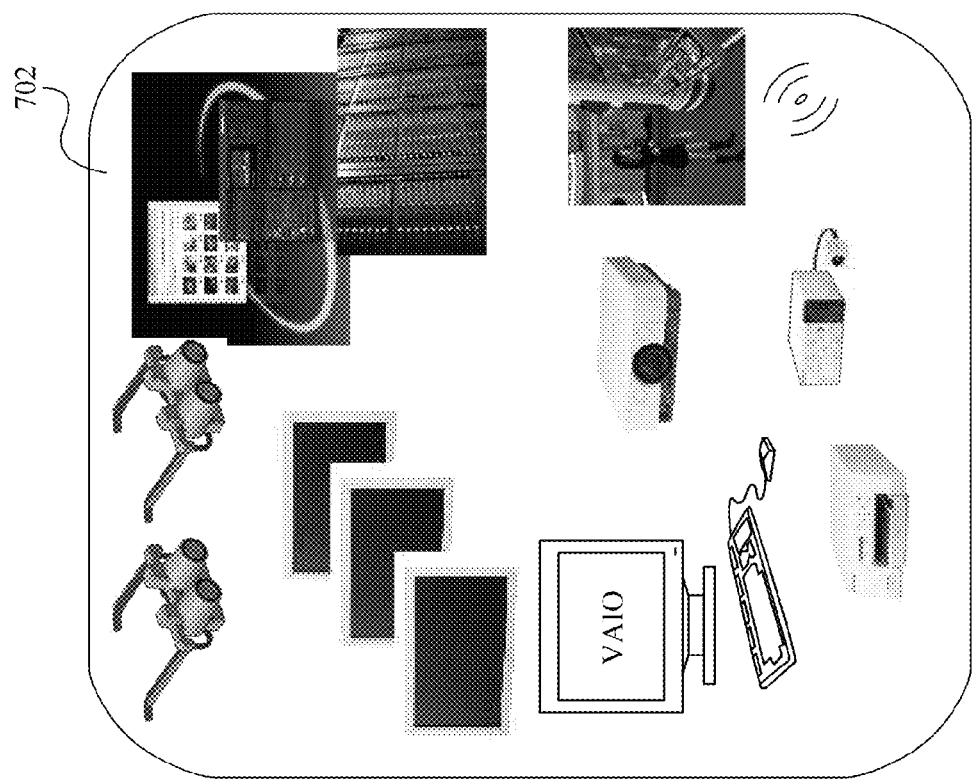
FIG. 7 illustrates packages of wireless loupe systems according to some embodiments.
Figure 7:
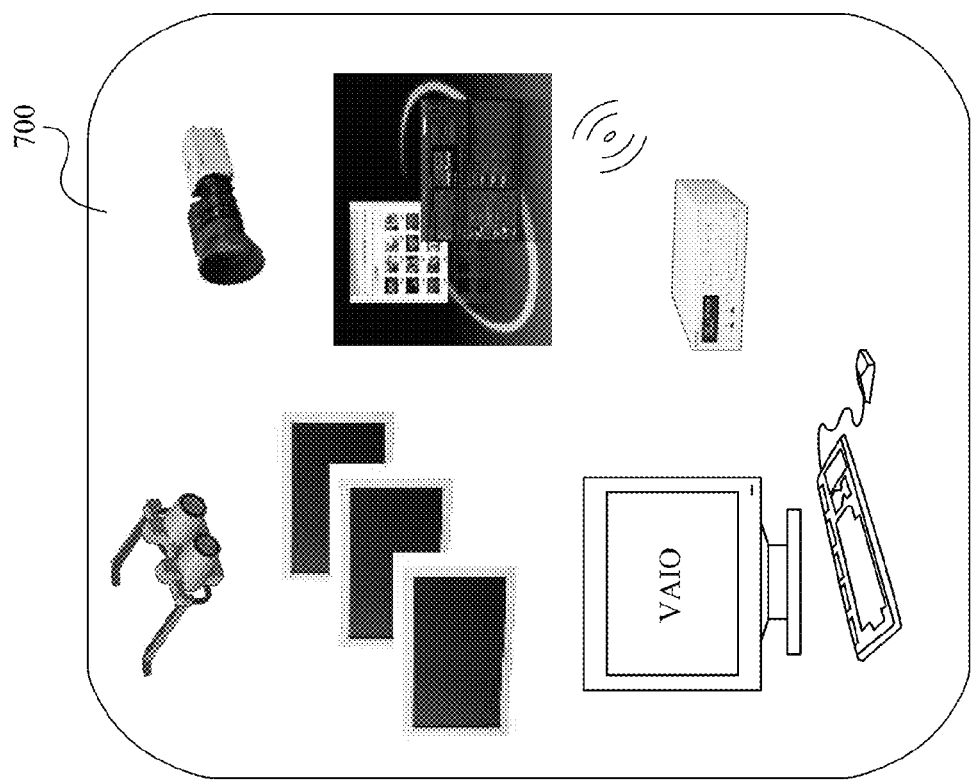

FIG. 7 illustrates packages of wireless loupe systems according to some embodiments. In an operating room package 700, a single wireless loupe is used in conjunction with an HD video camera, a monitor, televisions, the Internet, an HD video recorder and wi-fi. In a teaching hospital package, 702, two or more wireless loupes are used with a monitor, televisions, cloud computing, a projector, a digital color printer, an HD video recorder and wi-fi.

Figure 8:
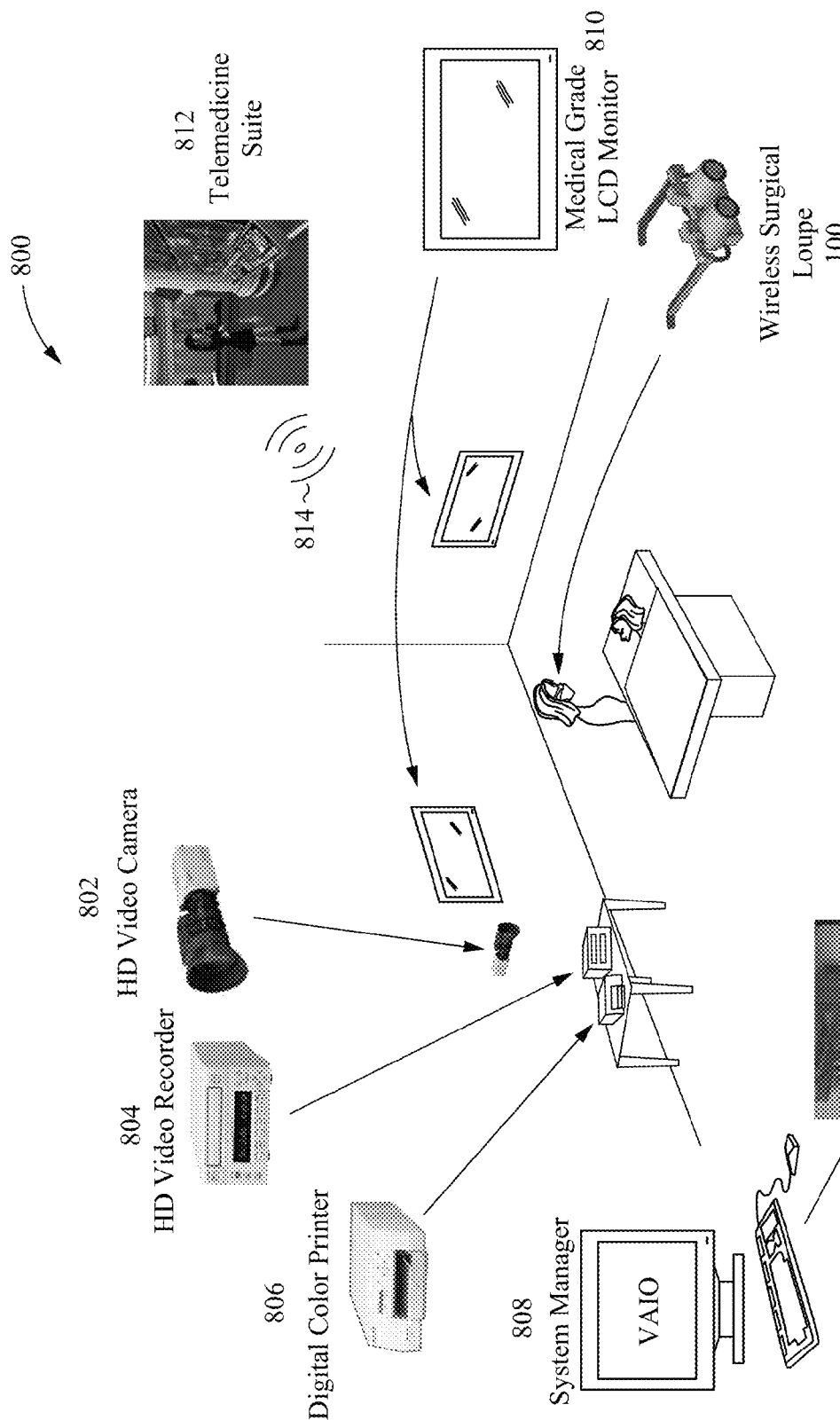
FIG. 8 illustrates a view of a wireless loupe system in an operating room according to some embodiments.

FIG. 8 illustrates a view of a wireless loupe system in an operating room according to some embodiments. For example, the wireless loupe system 800 includes a wireless loupe 100, an HD video camera 802, an HD video recorder 804, a digital color printer 806, a system manager device 808, two medical grade LCD monitors 810 and a telemedicine suite 812 which are all able to communicate using wi-fi 814 or any other wireless communication.

Figure 9:
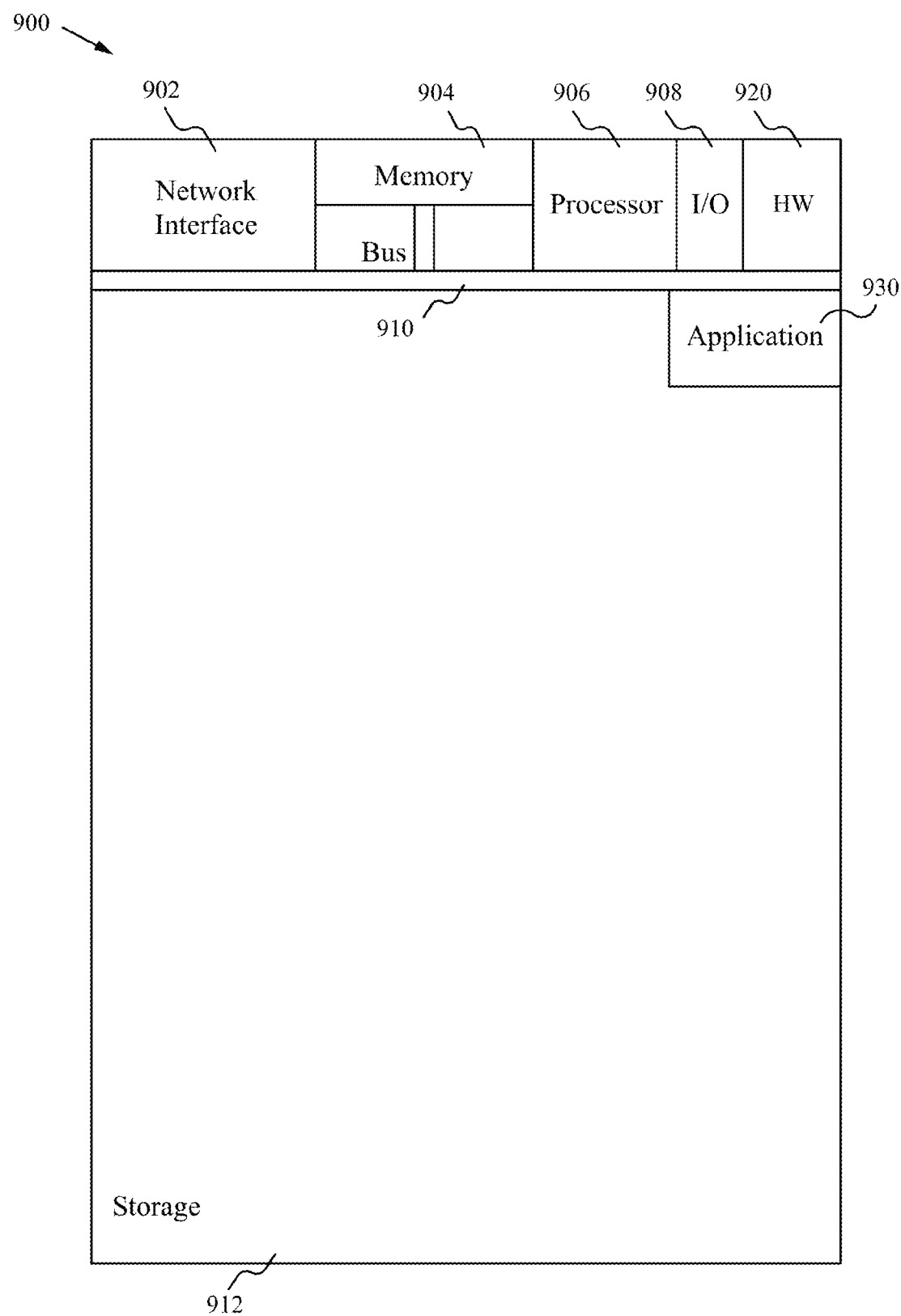
FIG. 9 illustrates a block diagram of an exemplary computing device configured to implement the wireless loupe method according to some embodiments.

FIG. 9 illustrates a block diagram of an exemplary computing device 900 configured to implement the wireless loupe method according to some embodiments. The computing device 900 is able to be used to acquire, store, compute, process, communicate and/or display information such as images, videos and patient data. In general, a hardware structure suitable for implementing the computing device 900 includes a network interface 902, a memory 904, a processor 906, I/O device(s) 908, a bus 910 and a storage device 912. The choice of processor is not critical as long as a suitable processor with sufficient speed is chosen. The memory 904 is able to be any conventional computer memory known in the art. The storage device 912 is able to include a hard drive, CDROM, CDRW, DVD, DVDRW, flash memory card or any other storage device. The computing device 900 is able to include one or more network interfaces 902. An example of a network interface includes a network card connected to an Ethernet or other type of LAN. The I/O device(s) 908 are able to include one or more of the following: keyboard, mouse, monitor, screen, printer, modem, touchscreen, button interface and other devices. Wireless loupe application(s) 930 used to perform the wireless loupe method are likely to be stored in the storage device 912 and memory 904 and processed as applications are typically processed. More or less components shown in FIG. 9 are able to be included in the computing device 900. In some embodiments, wireless loupe hardware 920 is included. Although the computing device 900 in FIG. 9 includes applications 930 and hardware 920 for the wireless loupe, the wireless loupe method is able to be implemented on a computing device in hardware, firmware, software or any combination thereof. For example, in some embodiments, the wireless loupe applications 930 are programmed in a memory and executed using a processor. In another example, in some embodiments, the wireless loupe hardware 920 is programmed hardware logic including gates specifically designed to implement the wireless loupe method.

In some embodiments, the wireless loupe application(s) 930 include several applications and/or modules. In some embodiments, modules include one or more sub-modules as well. In some embodiments, fewer or additional modules are able to be included.

Examples of suitable computing devices include a personal computer, a laptop computer, a computer workstation, a server, a mainframe computer, a handheld computer, a personal digital assistant, a cellular/mobile telephone, a smart appliance, a gaming console, a digital camera, a digital camcorder, a camera phone, a smart phone, a portable music player, a tablet computer, a mobile device, a video player, a video disc writer/player (e.g., DVD writer/player, Blu-ray® writer/player), a television, a home entertainment system or any other suitable computing device.

Figure 10:
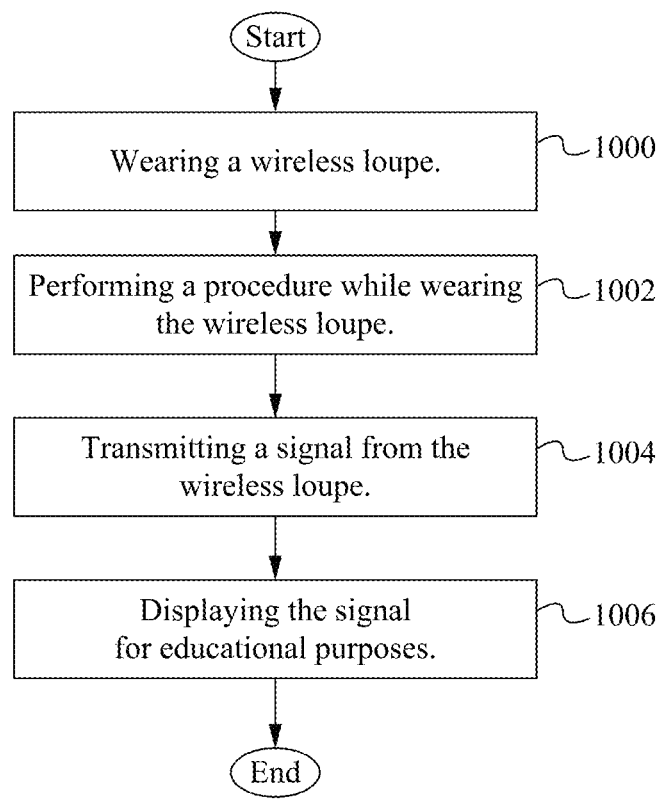
FIG. 10 illustrates a flowchart of a method of utilizing a wireless surgical loupe according to some embodiments.

FIG. 10 illustrates a flowchart of a method of utilizing a wireless surgical loupe according to some embodiments. In the step 1000, a user (e.g., a surgeon) wears a wireless surgical loupe. In the step 1002, the user performs a procedure (e.g., an operation) while wearing the wireless loupe. During the procedure, information such as patient vital information is displayed to the surgeon using a wireless loupe display. For example, the information received through the lens passes through a half mirror to the surgeon's eye, and the information is also reflected to an imager for acquiring the information. Additionally, patient information is displayed on a display which is reflected to the surgeon's eye by the half mirror as well as received at the imager for acquisition. In the step 1004, a signal is transmitted from the wireless loupe. The signal is able to be transmitted to an image processing system and/or any other device. In the step 1006, the signal is presented for educational purposes. In some embodiments, fewer or additional steps are implemented. In some embodiments, the order of the steps is able to be modified.

Figure 11:
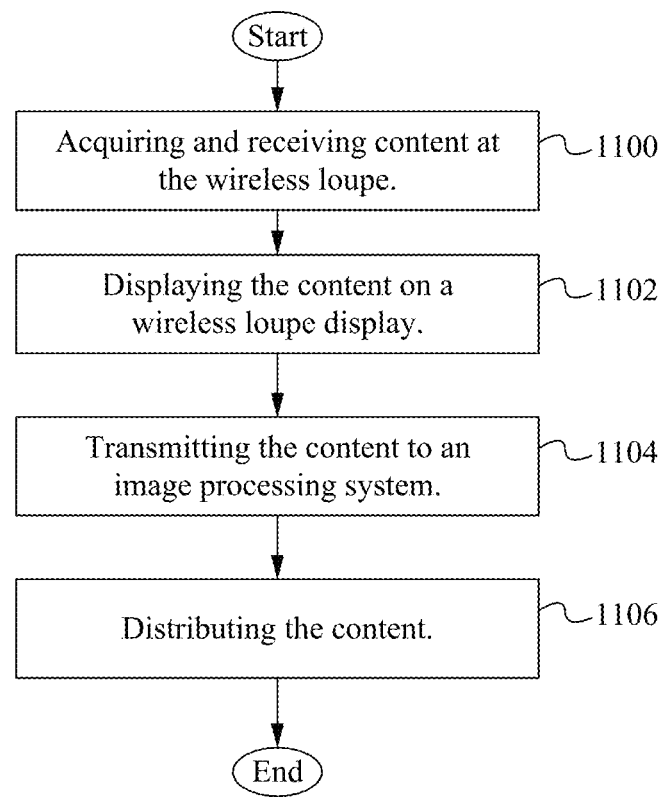
FIG. 11 illustrates a flowchart of a method of utilizing a wireless surgical loupe according to some embodiments.

FIG. 11 illustrates a flowchart of a method of utilizing a wireless surgical loupe according to some embodiments. In the step 1100, content is acquired and received at the wireless surgical loupe. Acquiring content includes receiving a signal of viewing a subject (e.g., a patient). In some embodiments, acquiring content includes light passing through a lens which is then split at a half mirror, with most of the light going directly to the user's eye, and the remainder of the light being acquired at a sensor. In some embodiments, receiving content includes receiving information from monitoring devices (e.g., a blood pressure monitor), the content being displayed on a display, and then the displayed information being split by the half mirror with part of the displayed information going to the user's eye, and part of the displayed information going to the sensor for acquisition. In the step 1102, the content is viewed by a user. For example, patient statistics are displayed on the wireless loupe display while the user is able to view a subject through the lens. In the step 1104, the acquired content and the received content (e.g., content acquired through the lens and content received by additional devices) are transmitted to an image processing system or another device wirelessly. For example, the scene that the user is viewing through the wireless loupe is recorded as images and/or a video at the image processing system. In some embodiments, the patient statistics are also recorded with the recorded viewed content. In the step 1106, the content is distributed. For example, the content is sent to other screens or monitors for educational purposes, for recording to be stored with the user's file and for any other purpose. In some embodiments, fewer or additional steps are implemented. In some embodiments, the order of the steps is able to be modified.

In some embodiments, the wireless surgical loupe includes features such as a 2D and/or 3D display, autofocus and zoom and a head mountable option. Since each lens is able to separately capture information, two simultaneous images are able to be acquired which are then able to be used to generate a 3D image.

To utilize the wireless surgical loupe, a user wears the loupe which receives and transmits information to be recorded. The process occurs automatically while the user is wearing the loupe.

In operation, the wireless surgical loupe, enables a user such as a surgeon to perform a procedure and record the procedure for educational, preservation and/or any other purposes. The wireless loupe also displays patient information and/or any other information to the surgeon so that the surgeon is able to track the patient more easily. The wireless surgical loupe system distributes the information such as a video of an operation, so that others are able to view the procedure remotely or record the information. Since 70% of the light passes through the half mirror to the surgeon, the surgeon is able to continue performing a procedure even if a power outage occurs.

Some Embodiments of a Wireless Surgical Loupe

1. A method of utilizing a wireless loupe, comprising:
   a. wearing the wireless loupe;
   b. displaying patient information on a display of the wireless loupe; and
   c. performing a procedure while wearing the wireless loupe.
2. The method of clause 1 wherein the wireless loupe is configured for automatically transmitting a signal including information acquired through a wireless loupe lens and the patient information to an external device.
3. The method of clause 2 further comprising presenting the signal for educational purposes.

4. A method of utilizing a wireless loupe, comprising:
   a. acquiring and receiving content at the wireless loupe;
   b. displaying the content on a wireless loupe display;
   c. transmitting the content to an image processing system; and
   d. distributing the content from the image processing system.
5. The method of clause 4 wherein the content comprises acquired content acquired through a lens and received content received from a separate medical device.
6. The method of clause 4 wherein acquiring the content includes receiving a signal of a subject.
7. The method of clause 4 wherein receiving the content includes receiving monitoring information from one or more monitoring devices.
8. The method of clause 7 wherein the monitoring information is displayed on the wireless loupe display.
9. The method of clause 7 wherein the monitoring information includes patient statistics.
10. The method of clause 4 wherein acquiring the content includes splitting the content using a half mirror, wherein a first portion of the content is viewable by a person and a second portion of the content is captured by a sensor.
11. The method of clause 4 wherein receiving the content includes displaying received content from a medical device and splitting the content using a half mirror, wherein a first portion of the content is viewable by a person and a second portion of the content is captured by a sensor.
12. The method of clause 4 wherein the image processing system records the content.
13. The method of clause 4 wherein transmitting is performed wirelessly.
14. The method of clause 4 wherein distributing the content includes sending the content to screens for educational purposes.
15. A wireless loupe device comprising:
   a. a lens;
   b. a half mirror for splitting information received from the lens into a first portion and a second portion, wherein the first portion goes to a user's eye and the second portion goes a sensor; and
   c. a wireless communication component for transmitting the information acquired at the sensor.
16. The wireless loupe device of clause 15 wherein the half mirror comprises translucent mirror technology.
17. The wireless loupe device of clause 15 further comprising a projection system for projecting patient information on a display which is split and reflected by the half mirror to the user's eye and received at the sensor.
18. A wireless loupe system comprising:
   a. a wireless loupe device for acquiring a first content, receiving a second content and transmitting the first content and the second content, wherein the first content includes information received through a lens of the wireless loupe device and the second content includes patient information from one or more monitoring devices; and
   b. an imaging system for receiving the first content and the second content.
19. The wireless loupe system of clause 18 wherein the imaging system is further for processing and storing the first content and the second content.
20. The wireless loupe system of clause 18 further comprising an internal network for distributing the first content and the second content to a medical recording device.
21. The wireless loupe system of clause 18 further comprising an external network for distributing the first content and the second content to one or more external screens.
22. The wireless loupe system of clause 18 wherein the wireless loupe device presents a through-the-lens view and the patient information.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:
1. A method of utilizing a wireless loupe, comprising:
   a. wearing the wireless loupe;
   b. acquiring and receiving content at the wireless loupe, including patient information and acquired content through a lens of the wireless loupe, wherein acquiring the content includes capturing two simultaneous images through separate lenses of the wireless loupe, and the two simultaneous images are used to generate a three dimensional image, wherein acquiring the content includes splitting the content using a half mirror, wherein a first portion of the content is viewable by a person and a second portion of the content is sent to an imaging optical system including one or more lenses which focus the second portion of the content onto a sensor, wherein the half mirror is configured to allow approximately 70% of light containing the first portion of the content to pass to the person;
   c. enhancing the acquired content by filtering information and highlighting information, wherein filtering the information includes removing a first part of the information to emphasize a second part of the information;
   d. displaying patient information on a display of the wireless loupe; and
   e. performing a procedure while wearing the wireless loupe.
2. The method of claim 1 wherein the wireless loupe is configured for automatically transmitting a signal including information acquired through the wireless loupe lenses and the patient information to an external device.
3. The method of claim 2 further comprising presenting the signal for educational purposes.
4. A method of utilizing a wireless loupe, comprising:
   a. acquiring and receiving content at the wireless loupe, wherein acquiring the content includes capturing two simultaneous images through separate lenses of the wireless loupe, and the two simultaneous images are used to generate a three dimensional image, wherein acquiring the content includes splitting the content using a half mirror, wherein a first portion of the content is viewable by a person and a second portion of the content is sent to an imaging optical system including one or more lenses which focus the second portion of the content onto a sensor, wherein the half mirror is configured to allow approximately 70% of light containing the first portion of the content to pass to the person;
   b. enhancing the content by filtering information and highlighting information, wherein filtering the information includes removing a first part of the information to emphasize a second part of the information;

c. displaying the enhanced content on a wireless loupe display;
d. transmitting the content to an image processing system; and
e. distributing the content from the image processing system.

5. The method of claim 4 wherein the content comprises acquired content acquired through the lenses and received content received from a separate medical device.

6. The method of claim 4 wherein acquiring the content includes receiving a signal of a subject.

7. The method of claim 4 wherein receiving the content includes receiving monitoring information from one or more monitoring devices.

8. The method of claim 7 wherein the monitoring information is displayed on the wireless loupe display.

9. The method of claim 7 wherein the monitoring information includes patient statistics.

10. The method of claim 4 wherein receiving the content includes displaying received content from a medical device and splitting the content using the half mirror, wherein the first portion of the content is viewable by the person and the second portion of the content is captured by the sensor.

11. The method of claim 4 wherein the image processing system records the content.

12. The method of claim 4 wherein transmitting is performed wirelessly.

13. The method of claim 4 wherein distributing the content includes sending the content to screens for educational purposes.

14. A wireless loupe device comprising:
a. lenses;
b. half mirrors for splitting information received from the lenses into a first portion and a second portion, wherein the first portion goes to a user's eye and the second portion goes to an imaging optical system including one or more lenses which focus the second portion of the content onto a sensor, wherein the second portion is enhanced by filtering information and highlighting information, wherein filtering the information includes removing a first part of the information to emphasize a second part of the information, wherein each of the second portion is acquired simultaneously and is used to generate a three dimensional image, wherein the half mirrors are configured to allow approximately 70% of light containing the first portion to pass to the person; and
c. a wireless communication component for transmitting the information acquired at the sensor.

15. The wireless loupe device of claim 14 wherein the half mirror comprises translucent mirror technology.

16. The wireless loupe device of claim 14 further comprising a projection system for projecting patient information on a display which is split and reflected by the half mirror to the user's eye and received at the sensor.

17. A wireless loupe system comprising:
a. a wireless loupe device for acquiring a first content, receiving a second content and transmitting the first content and the second content, wherein the first content includes information received through separate lenses of the wireless loupe device and the second content includes patient information from one or more monitoring devices, wherein the first content is enhanced by filtering information, highlighting information and utilizing image fusion, wherein acquiring the first content includes capturing two simultaneous images through the separate lenses of the wireless loupe, and the two simultaneous images are used to generate a three dimensional image, wherein acquiring the first content includes splitting the content using a half mirror, wherein a first portion of the first content is viewable by a person and a second portion of the content is sent to an imaging optical system including one or more lenses which focus the second portion of the first content onto a sensor, wherein the half mirror is configured to allow approximately 70% of light containing the first portion of the first content to pass to the person, further wherein the second portion of the first content is viewable by the person; and
b. an imaging system for receiving the first content and the second content.

18. The wireless loupe system of claim 17 wherein the imaging system is further for processing and storing the first content and the second content.

19. The wireless loupe system of claim 17 further comprising an internal network for distributing the first content and the second content to a medical recording device.

20. The wireless loupe system of claim 17 further comprising an external network for distributing the first content and the second content to one or more external screens.

21. The wireless loupe system of claim 17 wherein the wireless loupe device presents a through-the-lens view and the patient information.

* * * * *